US006683178B2

(12) United States Patent
Ohlbach et al.

(10) Patent No.: US 6,683,178 B2
(45) Date of Patent: Jan. 27, 2004

(54) PREPARATION OF CYCLIC LACTAMS

(75) Inventors: Frank Ohlbach, Dossenheim (DE);
Andreas Ansmann, Wiesloch (DE);
Peter Bassler, Viernheim (DE);
Rolf-Hartmuth Fischer, Heidelberg (DE); Hermann Luyken, Ludwigshafen (DE); Stefan Maixner, Schwetzingen (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/257,877

(22) PCT Filed: Apr. 30, 2001

(86) PCT No.: PCT/EP01/04833

§ 371 (c)(1),
(2), (4) Date: Oct. 17, 2002

(87) PCT Pub. No.: WO01/83441

PCT Pub. Date: Nov. 8, 2001

(65) Prior Publication Data

US 2003/0114664 A1 Jun. 19, 2003

(30) Foreign Application Priority Data

May 3, 2000 (DE) .......................... 100 21 201

(51) Int. Cl.$^7$ .......................................... C07D 201/08
(52) U.S. Cl. ...................................... 540/539
(58) Field of Search .......................... 540/539

(56) References Cited

U.S. PATENT DOCUMENTS

| 5,646,277 | A | | 7/1997 | Fuchs et al. ............... 540/539 |
| 6,100,396 | A | * | 8/2000 | Gayet et al. ............... 540/539 |
| 6,147,208 | A | | 11/2000 | Achammer et al. ......... 540/538 |
| 6,262,259 | B1 | * | 7/2001 | Cotting et al. .............. 540/539 |

FOREIGN PATENT DOCUMENTS

| EP | 826 665 | 3/1998 |
| EP | 826 666 | 3/1998 |
| GB | 1121109 | 7/1968 |
| WO | 95/14664 | 6/1995 |
| WO | 98/17642 | 4/1998 |

* cited by examiner

*Primary Examiner*—Bruck Kifle
(74) *Attorney, Agent, or Firm*—Keil & Weinkauf

(57) ABSTRACT

The invention relates to a method for producing cyclic lactams of formula (II) by reacting a compound (I) of formula (I) with water in the presence of an organic, liquid dilution agent in the liquid phase. In formula (II), n and m respectively can have the values 0, 1, 2, 3, 4, 5, 6, 7, 8 and 9 and the sum of n+m is at least 3, preferably at least 4 and $R^1$ and $R^2$ represent $C_1$–$C_6$ alkyl, $C_5$–$C_7$ cycloalkyl or $C_6$–$C_{12}$ aryl groups. In formula (I), $R^1$, $R^2$, m and n are defined as above and R represents nitrile, carboxylic acid amide and carboxylic acid groups. The inventive method is characterized in that a) compound (I) is reacted with water in the liquid phase in the presence of an organic, liquid dilution agent (III) to form a mixture (IV) containing a lactam (II) and said mixture (IV) is subjected to an aqueous treatment to obtain a two-phase system.

28 Claims, No Drawings

PREPARATION OF CYCLIC LACTAMS

SUMMARY

A process for the preparation of cyclic lactams of formula (II)

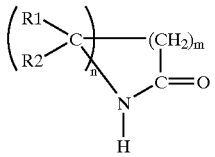
(II)

in which n and m may individually have the value 0, 1, 2, 3, 4, 5, 6, 7, 8 or 9 and the sum of n and m is at least 3 and preferably at least 4 and $R^1$ and $R^2$ denote $C_1$–$C_6$ alkyl, $C_5$–$C_7$ cycloalkyl or $C_6$–$C_{12}$ aryl groups by the reaction of a compound (I) of the formula

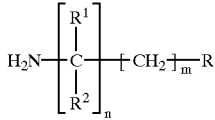
(I)

in which $R^1$, $R^2$, m and n have the meanings stated above and R de-notes nitrile, carboxamide and carboxylic acid groups, with water in the presence of an organic liquid diluent in the liquid phase, wherein a) compound (I) is caused to react with water in the liquid phase in the presence of an organic liquid diluent (III) to form a mixture (IV) containing a lactam (II), the diluent (III) having a miscibility gap with water under certain conditions of concentration, pressure and temperature, b) mixture (IV) is subjected, before or after separation of ammonia, to conditions of concentration, pressure and temperature under which diluent (III) and water are present in the liquid state and exhibit a miscibility gap, to give a two-phase system comprising a phase (V) in which the content of diluent (III) is higher than that of water and a phase (VI) in which the content of water is higher than that of diluent (III), c) phase (V) is separated from phase (VI), and d) from phase (V) diluent (III) and optionally by-products comprising low boilers, high boilers and/or unconverted compound (I) are separated, to give lactam (II).

DESCRIPTION

The present invention relates to a process for the preparation of cyclic lactams of formula (II)

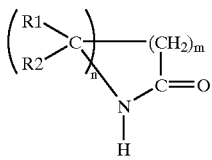
(II)

in which n and m may individually have the value 0, 1, 2, 3, 4, 5, 6, 7, 8 or 9 and the sum of n+m is at least 3 and preferably at least 4, and $R^1$ and $R^2$ denote $C_1$–$C_6$ alkyl, $C_5$–$C_7$ cycloalkyl or $C_6$–$C_{12}$ aryl, by the reaction of a compound (I) of the formula

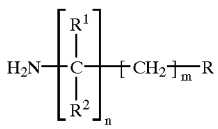
(I)

in which $R^1$, $R^2$, m and n have the meanings stated above and R denotes nitrile, carboxamide and carboxylic acid groups, with water in the presence of an organic liquid diluent in the liquid phase, wherein a) compound (I) is caused to react with water in the liquid phase in the presence of an organic liquid diluent (III) to form a mixture (IV) containing a lactam (II), the diluent (III) having a miscibility gap with water under certain conditions of concentration, pressure and temperature, b) mixture (IV) is subjected, before or after separation of ammonia, to conditions of concentration, pressure and temperature under which diluent (III) and water are present in the liquid state and exhibit a miscibility gap, to give a two-phase system comprising a phase (V) in which the content of diluent (III) is higher than that of water and a phase (VI) in which the content of water is higher than that of diluent (III), c) phase (V) is separated from phase (VI), and d) from phase (V) diluent (III) and optionally by-products comprising low boilers, high boilers and/or unconverted compound (I) are separated, to give lactam (II).

Processes for the preparation of cyclic lactams by reaction of ω-aminocarboxylic derivatives with water in the presence of a heterogeneous catalyst and an organic liquid diluent in the liquid phase are well known, for example the preparation of caprolactam from 6-aminocarboxynitrile.

Thus WO 95/14665 and WO 95/14664 disclose that it is possible to cause 6-aminocapronitrile to react in the liquid phase with water in the presence of heterogeneous catalysts and a solvent to form caprolactam and ammonia. The highest caprolactam yields (from 86 to 94%) are attained using titanium(IV) oxide as catalyst and ethanol as solvent. The caprolactam yields were determined only by gas chromatography and workup of the effluents to produce crude and/or pure caprolactam is not described.

WO 97/23454 describes, in Example 1C, the reaction of 6-aminocapronitrile with water in the presence of titanium (IV) oxide and ethanol. Caprolactam was obtained from the effluent by fractional distillation in a yield of 80%.

A disadvantage of the said conversion of 6-aminocapronitrile to caprolactam in the presence of ethanol is that the caprolactam yields are low. The yield losses occurring during workup are not indicated.

It is thus an object of the present invention to provide a process which allows for the preparation of cyclic lactams (II) from compounds (I) in an industrially simple and economical manner to give high conversions of compound (I) and high lactam yields and minimizes yield losses during the purification stage.

Thus we have found the process defined above.

Suitable compounds (I) are amino acids and their derivatives, preferably those of the general formula I

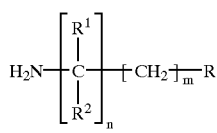

in which R denotes a carboxylic acid group, a nitrile group and/ or a carboxamide group and n and m independently have a value of 0, 1, 2, 3, 4, 5, 6, 7, 8 or 9 and the sum of n+m is at least 3 and preferably at least 4.

$R^1$ and $R^2$ can be theoretically substituents of any type, the only proviso being that the desired cyclization reaction may not be influenced by the substituents. $R^1$ and $R^2$ are preferably independently $C_1$–$C_6$ alkyl or $C_5$–$C_7$ cycloalkyl or $C_6$–$C_{12}$ aryl groups.

Particularly preferred starting compounds are aminocarboxynitriles, preferably of the general formula

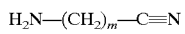

in which m has a value of 3, 4, 5 or 6 and particularly 5. When m is 5, the starting compound is 6-aminocapronitrile.

The compound (I) used can be an individual compound (I) or a mixture of different compounds (I). Preferably compound (I) is used as an individual compound.

ω-Aminocarboxynitriles are obtained, for example, by partial hydrogenation of α, ω-dinitriles in the vapor or liquid phase, eg as described in WO 96/20166, WO 96/20916 or WO 96/20165.

ω-Amino acids are obtained, for example, by hydroamination of ω-formylcarboxylic acids or by hydrolysis of ω-aminocarboxylates or ω-aminocarboxynitriles.

ω-Amino acids are obtained, for example, by hydroamination of ω-formylcarboxylic acids or hydrolysis of ω-aminocarboxylates or ω-aminocarboxynitriles.

In the process of the invention there are obtained, depending on compound (I), the corresponding cyclic lactams of formula (II)

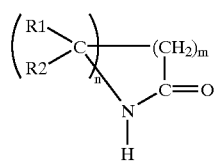

in which n, m, $R^1$ and $R^2$ have the meanings stated above. Particularly preferred lactams are those in which n is equal to 0 and m has a value of 3, 4, 5 or 6. When m is 5, the product is caprolactam.

In the process of the invention the compound (I) described above is caused to react, in step a), with water in the liquid phase, preferably in a homogeneous liquid phase, advantageously in the presence of a heterogeneous catalyst and an organic liquid diluent (III), to form a mixture (IV) containing a lactam (II), the diluent (III) exhibiting a miscibility gap with water under certain conditions of concentration, pressure and temperature.

Suitable heterogeneous catalysts are acid, basic or amphoteric oxides of Group IIa, Group IIIa or Group IVa elements, such as calcium oxide, magnesium oxide, boron oxide, aluminum oxide, tin oxide or silicon dioxide as pyrogenically prepared silicon dioxide, as silica gel, kieselguhr, quartz or mixtures thereof, also oxides of Group IIb to Group VIb metals, such as amorphous titanium(IV) oxide as anatase or rutile, zirconium dioxide, manganese oxide or mixtures thereof. Also useful are oxides of the lanthanoids and actinides, such as cerium oxide, thorium oxide, praseodymium oxide, samarium oxide, rare-earth mixed oxide, or mixtures thereof with the above oxides. Examples of further catalysts are:

vanadium oxide, barium oxide, zinc oxide, niobium oxide, iron oxide, chromium oxide, molybdenum oxide, tungsten oxide or mixtures thereof.

Mixtures of said oxides with each other are likewise possible. In addition, some sulfides, selenides and tellurides such as zinc telluride, tin selenide, molybdenum sulfide, tungsten sulfide, and sulfides of nickel, zinc and chromium can be used.

The aforementioned compounds can be doped with, or contain, Group 1a compounds and Group 7a compounds.

Examples of other suitable catalysts are zeolites, phosphates and heteropoly acids, and also acid and alkaline ion exchangers such as Naflon.

Preferred catalysts are titanium oxide, aluminum oxide, cerium oxide and zirconium dioxide and more preferred catalysts are titanium(IV) oxides such as are disclosed in, for example, WO 96/36600. The preparation of such catalysts as shaped articles is described, for example, in WO 99/11613, WO 99/11614 and WO 99/11615.

Suitable diluents (III) are $C_4$–$C_9$ alkanols, such as n-butanol, isobutanol and n-pentanol, preferably aliphatic hydrocarbons, such as hexane, alicyclic hydrocarbons, such as cyclopentane or cyclohexane, particularly aromatic hydrocarbons, such as benzene, toluene, o-xylene, m-xylene, p-xylene, ethylbenzene, isopropylbenzene, di-isopropylbenzene and mixtures of such compounds, for example petroleum ether. The hydrocarbons can carry functional groups, such as halogens, for example chlorine, as in chlorobenzene.

During the reaction in step a) ammonia may be present.

During the reaction in step a), generally at least 0.1 mol, preferably from 0.5 to 50 mol and more preferably from 1 to 20 mol of water should be used per mol of compound (I).

Advantageously, in step a), the percentage of compound (I) in the total starting components compound (I), water and diluent (III) is from 0.1 to 50 wt %, preferably from 1 to 30 wt % and more preferably from 2 to 20 wt %.

The reaction can be advantageously carried out at temperatures generally ranging from 140° to 320° C., preferably from 180° to 300° C. and more preferably from 200° to 280° C., in liquid phase. The pressure should generally be in the range of from 1 to 250 bar and preferably from 5 to 150 bar.

The pressure and temperature conditions preferred are those under which the reaction mixture is a single homogeneous liquid phase.

The space velocities are generally in the range of from 0.05 to 5 kg, preferably from 0.1 to 2 kg and more preferably from 0.2 to 1 kg of reaction mixture per liter of catalyst per hour.

The reaction of step a) produces a mixture (IV), which contains a lactam (II).

If mixture (IV) contains ammonia, the separation of ammonia from the mixture (IV) in step b) can take place after, but preferably prior to, phase separation, preferably by distillation, to give a mixture (IX) containing no or little ammonia. Separation of the ammonia can take place, if desired, following phase separation, preferably by distillation, from phase (V) and/or phase (VI).

Mixture (IV) can contain ammonia, for example if ammonia is formed during the reaction taking place in step a) and/or ammonia was added to the reaction mixture used in step a). Ammonia can be formed during the reaction of step a) for example when R is a nitrile or carboxamide group.

Separation can advantageously be carried out by distillation, particularly at base temperatures ranging from 60° to 220° C. and pressures ranging from 1 to 30 bar.

If mixture (IV) contains no ammonia, by which we include traces of ammonia too small to be of detriment to the succeeding process steps, mixture (IV) and mixture (IX) will be identical.

As specified for step b), mixture (IX) is subjected, according to the invention, to conditions of concentration, pressure and temperature under which diluent (III) and water are present in the liquid state and exhibit a miscibility gap, to give a two-phase system comprising phase (V) and phase (VI).

Preference is given to such conditions of concentration, pressure and temperature as allow the constituents of mixture (VII) to be present in phases (V) and (VI) in a wholly liquid state, ie with no occurrence of precipitation of solid matter.

If step a) is carried out in a homogeneous liquid phase, separation of mixture (VII) into the two phases (V) and (VI) can generally be achieved by appropriate selection of a suitable temperature. Another possibility is to select suitable proportions or to add diluent (III), preferably water.

Phase (V) and phase (VI) are then separated in accordance with the invention as specified for step c).

Phase separation can be carried out in known manner in apparatus known to be suitable for such a purpose, as described, for example, in Ullmann's Encyclopedia of Industrial Chemistry, Vol. B3, 5th Edition, VCH verlagsgesellschaft, Weinheim, 1988, page 6–14 to 6–22.

The apparatus and process conditions most suitable for this phase separation can be readily found by carrying out a few simple preliminary tests.

In step d), diluent (III) and optionally ammonia and optionally by-products comprising low boilers (VIII), high boilers (VII) and/or unconverted compound (I) are, according to the invention, separated from phase (V) to give lactam (II).

By low boilers (VIII) we mean, for the purposes of the present invention, compounds having a boiling point below that of lactam (II), and by high boilers (VII) compounds having a boiling point above that of lactam (II).

Purification can be advantageously carried out by fractional distillation in one or more, such as 2 or 3, distillation assemblies.

Suitable apparatus for the distillation comprises conventional apparatus, as described, for example, in Kirk-Othmer, Encyclopedia of Chemical Technology, 3 Ed., Vol. 7, John Wiley & Sons, New York, 1979, pages 870–881, such as sieve-plate columns, bubble-cap columns, or packed columns.

Preferably, the first operation is to separate any ammonia still present and diluent (III) from phase (V). From lactam (II) there can then be separated high boilers (VII), low boilers (VIII) and any unconverted compound (I), individually or concurrently.

Advantageously, the diluent (III) that is separated in step d) can be partially or completely recycled to step a).

Advantageously, any high boilers (VIII) and/or low boilers (VII) separated in step d) can be recycled, partially or completely, to step a).

Advantageously, any unconverted compound (I) separated in step d) can be recycled, partially or completely, to step a).

The phase (VI) formed in step c) may be advantageously recycled to step a).

Preferably, lactam (II) can be partially or completely separated from phase (VI) to give a mixture (X) and from the resulting lactam (II) there may be separated any low boilers (VIII) and/or high boilers (VII).

Purification of lactam (II) can be advantageously carried out by fractional distillation in one or more, such as 2 or 3, distillation assemblies.

Suitable apparatus for the distillation comprises conventional apparatus, as described, for example, in Kirk-Othmer, Encyclopedia of Chemical Technology, 3 Ed., Vol. 7, John Wiley & Sons, New York, 1979, pages 870–881, such as sieve-plate columns, bubble-cap columns, or packed columns.

From lactam (II) there can be separated high boilers (VII) and/or low boilers (VIII), individually or concurrently.

Advantageously, the high boilers (VII) and/or low boilers (VIII) can be partially or completely recycled to step a).

The lactam (II) separated from phase (VI) can, prior to purification thereof, be combined with the crude lactam (II) separated in step d) and the resulting mixture then purified.

Advantageously phase (X) can be recycled to step a).

Separation of lactam (II) from phase (VI) may be effected by extraction with a liquid extracting agent (XI), partially or completely, to give a mixture (XII), which contains an extracting agent (XI) and a lactam (II).

Suitable extracting agents (XI) are $C_4$–$C_9$ alkanols, such as n-butanol, isobutanol and n-pentanol, preferably aliphatic hydrocarbons, such as hexane, alicyclic hydrocarbons, such as cyclopentane or cyclohexane, particularly aromatic hydrocarbons, such as benzene, toluene, o-xylene, m-xylene, p-xylene, ethylbenzene, isopropylbenzene, di-isopropylbenzene and also mixtures of such compounds, for example petroleum ether. The hydrocarbons can carry functional groups, such as halogens, for example chlorine, as in chlorobenzene.

In particular, extracting agent (XI) and diluent (III) have the same or a similar composition.

Thus the extracting agent (XI) can advantageously be diluent (III) separated in step d).

The aqueous phase (X) remaining after extraction can advantageously be recycled to step a).

Advantageously, extracting agent (XI) and any low boilers (VIII), high boilers (VII) and/or unconverted compound (I) can be separated from mixture (XII) to give lactam (II).

Purification can be advantageously carried out by fractional distillation in one or more, such as 2 or 3, distillation assemblies.

Suitable apparatus for the distillation comprises conventional apparatus, as described, for example, in Kirk-Othmer, Encyclopedia of Chemical Technology, 3 Ed., Vol. 7, John Wiley & Sons, New York, 1979, pages 870–881, such as sieve-plate columns, bubble-cap columns, or packed columns.

Preferably, separation of extracting agent (XI) from mixture (XII) is first carried out. From lactam (II) there can then be separated the high boilers, low boilers and any unconverted compound (I), individually or concurrently.

Advantageously, the extracting agent (XI) that is separated during purification can be partially or completely recycled to step a).

Advantageously, high boilers (VII) and/or low boilers (VIII) that may be separated during purification can be partially or completely recycled to step a).

Advantageously, any unconverted compound (I) that is delivered by the workup process can be partially or completely recycled to step a).

Advantageously, mixture (XII) and phase (V) can be used together in step d) of the process of the invention. Mixture (XII) and phase (V) can be combined before or during step d).

The lactams produced by the process of the invention can be used in known manner for the manufacture of industrially important polymers, such as polyamides.

EXAMPLES

Example 1

ACN Cyclization with LM Forming, on Cooling, Two Phases

A mixture of 80 g of solvent and 0.5 g of $TiO_2$ powder (100% anatase) is in each case used as initial batch in a stirred autoclave having a capacity of 270 ml, the reactor is heated to 270° C. and a mixture of 10 g of 6-aminocapronitrile and 10 g of water is then metered in over a period of one minute. After the elapse of different periods of time, 10 mL samples are taken in order to determine the best yield. The suspensions are in each case filtered, freed from solvent and analyzed by GC using an internal standard.

The results obtained using various solvents are listed in Table 1 below.

TABLE 1

| Solvent | Reaction time [min] | Conversion [%] | Caprolactam yield [%] |
|---|---|---|---|
| benzene | 300 | 99.6 | 96.1 |
| toluene | 300 | 98.6 | 96.1 |
| o-xylene | 360 | 99.8 | 96.0 |
| chlorobenzene | 180 | 99.5 | 94.9 |
| cyclohexane | 240 | 97.3 | 95.2 |
| cyclopentane | 260 | 98.0 | 95.4 |
| n-hexane | 300 | 98.9 | 97.7 |

Example 2

80 kg of 6-aminocapronitrile, 50 kg of water and 1200 kg of toluene were fed, per hour, to a tubular reactor having a capacity of 300 L and packed with 250 kg of catalyst (titanium(IV) oxide, 100% anatase).

The ammonia formed during the reaction was separated by distillation.

After cooling to 25° C., the aqueous phase was then separated from the organic phase and the organic phase purified by distillation.

There was obtained caprolactam as shown in Table 2.

Example 3

80 kg of 6-aminocapronitrile, 50 kg of water and 1200 kg of toluene were fed, per hour, to a tubular reactor having a capacity of 300 L and packed with 250 kg of catalyst (titanium(IV) oxide, 100% anatase).

The ammonia formed during the reaction was separated by distillation.

After cooling to 25° C., the aqueous phase was separated from the organic phase and the toluene separated from the organic phase to give a crude lactam.

The aqueous phase was extracted with half the amount of toluene, the phases were separated and the organic phase was combined with the crude lactam.

The combined mixture of crude lactam and organic phase was purified by distillation.

There was obtained caprolactam as shown in Table 2.

Example 4

80 kg of 6-aminocapronitrile, 50 kg of water and 1200 kg of toluene were fed, per hour, to a tubular reactor having a capacity of 300 L and packed with 250 kg of catalyst (titanium(IV) oxide, 100% anatase).

The ammonia formed during the reaction was separated by distillation.

After cooling to 25°0 C. the aqueous phase was separated from the organic phase; the aqueous phase was recycled to the reaction involving 6-aminocapronitrile, the amount of water being adjusted to 50 kg/h, and the organic phase was purified by distillation.

Under steady-state conditions caprolactam was obtained as shown in Table 2.

Example 5

80 kg of 6-aminocapronitrile, 50 kg of water and 1200 kg of toluene were fed, per hour, to a tubular reactor having a capacity of 300 L and packed with 250 kg of catalyst (titanium(IV) oxide, 100% anatase).

The ammonia formed during the reaction was separated by distillation.

After cooling to 25° C. the aqueous phase was separated from the organic phase; the aqueous phase was recycled to the reaction involving 6-aminocapronitrile, the amount of water being adjusted to 50 kg/h, and the organic phase was purified by distillation. The high boilers obtained by distillation (and having a caprolactam content of 30 wt %) were recycled to the reaction involving 6-aminocapronitrile.

Under steady-state conditions caprolactam was obtained as shown in Table 2.

Comparative Example 80 kg of 6-aminocapronitrile, 50 kg of water and 1200 kg of toluene were fed, per hour, to a tubular reactor having a capacity of 300 L and packed with 250 kg of catalyst (titanium(IV) oxide, 100% anatase).

The ammonia formed during the reaction was separated by distillation.

Then water and toluene were separated concurrently and the crude lactam was purified by distillation.

There was obtained caprolactam as shown in Table 2.

TABLE 2

| Examples | Caprolactam yield [%] | Low boilers [%] | High boilers [%] |
|---|---|---|---|
| 2 | 81.5 | 0.6 | 4.9 |
| 3 | 87.7 | 0.6 | 4.9 |
| 4 | 94.4 | 0.6 | 4.9 |
| 5 | 99.4 | 0.5 | — |
| Comp. Ex. | 71.6 | 0.6 | 27.8 |

In Examples 2–5 no drop in caprolactam yield was observed, not even after an on-stream time of more than 200 hours.

What is claimed is:

1. A process for the preparation of cyclic lactams of formula (II)

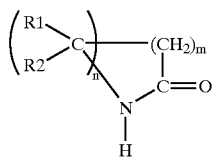
(II)

in which n and m can individually have a value of 0, 1, 2, 3, 4, 5, 6, 7, 8 or 9, the sum of n and m is at least 3 and $R^1$ and $R^2$ denote $C_1$–$C_6$ alkyl, $C_5$–$C_7$ cycloalkyl or $C_6$–$C_{12}$ aryl groups by the reaction of a compound (I) of the formula

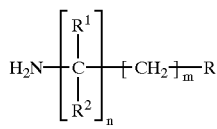
(I)

in which $R^1$, $R_2$, m and n have the meanings stated above and R denotes nitrile, carboxamido and carboxyl groups, with water in the presence of an organic liquid diluent in the liquid phase, wherein a) compound (I) is caused to react with water in the liquid phase in the presence of an organic liquid diluent (III) to form a mixture (IV) containing lactam (II), the diluent (III) having a miscibility gap with water under certain conditions of concentration, pressure and temperature, b) mixture (IV) is subjected, before or after separation of ammonia, to conditions of concentration, pressure and temperature under which diluent (III) and water are present in the liquid state and exhibit a miscibility gap, to give a two-phase system comprising a phase (V) in which the content of diluent (III) is higher than that of water and a phase (VI) in which the content of water is higher than that of diluent (III), c) phase (V) is separated from phase (VI), and d) from phase (V) diluent (III) and optionally by-products comprising low boilers, high boilers and/or unconverted compound (I) are separated, to give lactam (II).

2. A process as defined in claim 1, wherein the compound (I) used is an aminocapronitrile.

3. A process as defined in claim 1, wherein the compound (I) used is an aminocapronitrile of the formula $$NH_2-(CH_2)_m-CN$$

in which m is 3, 4, 5 or 6.

4. A process as defined in claim 1, wherein the compound (I) used is 6-aminocapronitrile.

5. A process as defined in claim 1, wherein step a) is carried out in the presence of a heterogeneous catalyst.

6. A process as defined in claim 5, wherein the heterogeneous catalyst used is titanium(IV) oxide, aluminum oxide, cerium oxide or zirconium dioxide.

7. A process as defined in claim 1, wherein the reaction in step a) is carried out at a temperature ranging from 140° to 320° C.

8. A process as defined in claim 1, wherein the sum of the concentrations of compound (I) and compound (II), based on mixture (IV), is less than 20 wt %.

9. A process as defined in claim 1, wherein the diluent (III) used is an aliphatic, cycloaliphatic or aromatic hydrocarbon.

10. A process as defined in claim 1, wherein the diluent (III) used is ethylbenzene, benzene, toluene, o-xylene, m-xylene or p-xylene.

11. A process as defined in claim 1, wherein separation of ammonia from mixture (IV) is carried out prior to separation of phase (V) specified for step c).

12. A process as defined in claim 1, wherein the reaction in step a) is carried out in a homogeneous liquid phase.

13. A process as defined in claim 1, wherein the phase (VI) separated in step c) is completely or partially recycled to step a).

14. A process as defined in claim 1, wherein from phase (VI), separated in step c) to give a phase (X) containing less lactam (II) than phase (VI), lactam (II) is partially or completely separated and from the resulting lactam (II) there are separated, optionally, any by-products comprising low boilers (VIII) and high boilers (VII).

15. A process as defined in claim 1, wherein from phase (VI) lactam (II) is partially or completely separated by extraction with an extracting agent (XI) to give a mixture (XII), containing extracting agent (XI) and lactam (II), and a phase (X), containing less lactam (II) than phase (VI).

16. A process as defined in claim 14, wherein phase (X) is completely or partially recycled to step a).

17. A process as defined in claim 15, wherein the extracting agent (XI) and any by-products comprising low boilers (VIII) and high boilers (VII) are separated from mixture (XII) to give lactam (II).

18. A process as defined in claim 15, wherein mixture (XII) and phase (V) are used concurrently in step d).

19. A process as defined in claim 15, wherein extracting agent (XI) and diluent (III) are one and the same or have the same composition.

20. A process as defined in claim 13, wherein lactam (II) is separated only from that partial stream of phase (VI) which is not recycled to the cyclization stage and the remaining portion of phase (VI) is completely or partially recycled to step a) without recovery of lactam (II).

21. A process as defined in claim 1, wherein unconverted compound (I) separated in step d) is partially or completely recycled to step a).

22. A process as defined in claim 1, wherein high boilers (VII) separated in step d) are completely or partially recycled to step a).

23. A process as defined in claim 22, wherein the high boilers (VII) separated in step d) contain at least 20 wt % of lactam (II).

24. A process as defined in claim 1, wherein diluent (III) separated in step d) is partially or completely recycled to step a).

25. A process as defined in claim 1, wherein low boilers (VIII) separated in step d) are partially or completely recycled to step a).

26. A process as defined in claim 15, wherein the extracting agent (XI) used is diluent (III) separated in step d).

27. A process as defined in claim 15, wherein lactam (II) is completely or partially extracted with water from phase (V) or phase (XII) to give a phase (XIII), containing a lesser amount of lactam (II), and a phase (XIV), containing a greater amount of lactam (II), and phase (XIII) is completely or partially recycled to step a).

28. A process as defined in claim 14, wherein the stream of high boilers (VII) recycled to step a) is combined with the recycled stream (VI) or (X) before reaching step a).

* * * * *